(12) United States Patent
Okazaki (10) Patent No.: US 9,713,512 B2
(45) Date of Patent: Jul. 25, 2017

(54) ORTHODONTIC DEVICE-SETTING TOOL (71) Applicant: Kazuyuki Okazaki, Kochi (JP)

(72) Inventor: Kazuyuki Okazaki, Kochi (JP)

( * ) Notice: Subject to any disclaimer, the term of this patent is extended or adjusted under 35 U.S.C. 154(b) by 0 days.

(21) Appl. No.: 14/371,930

(22) PCT Filed: Feb. 5, 2013

(86) PCT No.: PCT/JP2013/052524
§ 371 (c)(1),
(2) Date: Jul. 11, 2014

(87) PCT Pub. No.: WO2013/125340
PCT Pub. Date: Aug. 29, 2013

(65) Prior Publication Data
US 2014/0349241 A1 Nov. 27, 2014

(30) Foreign Application Priority Data

Feb. 20, 2012 (JP) ................................. 2012-033587

(51) Int. Cl.
*A61C 7/14* (2006.01)
(52) U.S. Cl.
CPC .................................... *A61C 7/146* (2013.01)
(58) Field of Classification Search
CPC ..................................................... A61C 7/146
(Continued)

(56) References Cited

U.S. PATENT DOCUMENTS 3,787,976 A * 1/1974 Cohen .................... A61C 7/146
433/3

4,284,405 A * 8/1981 Dellinger ............... A61C 7/146
433/24

(Continued)

FOREIGN PATENT DOCUMENTS

JP 11-99161 A 4/1999
JP 2003-532485 A 5/2003
(Continued)

OTHER PUBLICATIONS

International Search Report for International Application No. PCT/JP2013/052524, dated Feb. 22, 2013.

*Primary Examiner* — Nicholas Lucchesi
(74) *Attorney, Agent, or Firm* — Heslin Rothenberg Farley & Mesiti P.C.

(57) ABSTRACT

An orthodontic device-setting tool is provided with: a fitting section having a fitting surface, which covers and fits together with at least one of the incisal margin, the dental cusp, or the occlusal surface of a tooth; a foundation section, which has a back surface that adheres closely to the labial/buccal surface or the lingual surface of the tooth and has, on the surface opposite the back surface, a front face on which the orthodontic device is mounted; and a connecting section that connects the fitting section and the foundation section. The tool has a frame section, which protrudes from the front face of the foundation section and can fit together with the orthodontic device. Use of the orthodontic device-setting tool makes it possible to mount orthodontic devices such as corrective brackets without holding the patient for long periods of time and to mount the orthodontic devices accurately at the desired three-dimensional mounting positions for the orthodontic devices regardless of the skill level of the dentist practitioner. Moreover, the tool can even be used with mass-produced general purpose orthodontic devices, which are not orthodontic devices that have been specially customized as to design, cut, etc. for individual patients.

9 Claims, 9 Drawing Sheets (58) Field of Classification Search
USPC .................................................. 433/3, 9, 24
See application file for complete search history.

(56) References Cited

U.S. PATENT DOCUMENTS

| | | | | |
|---|---|---|---|---|
| 4,360,341 A * | 11/1982 | Dellinger | ............... | A61C 7/146 433/24 |
| 4,494,931 A * | 1/1985 | Wildman | ................ | A61C 7/12 433/3 |
| 4,523,908 A * | 6/1985 | Drisaldi | ................ | A61C 7/146 433/3 |
| 4,626,208 A * | 12/1986 | Hall | ..................... | G01S 13/755 433/3 |
| 5,064,369 A * | 11/1991 | Kawaguchi | ............ | A61C 7/146 433/3 |
| 5,863,198 A * | 1/1999 | Doyle | .................... | A61C 7/146 433/3 |
| 6,123,544 A * | 9/2000 | Cleary | .................. | A61C 7/146 433/24 |
| 6,554,613 B1 * | 4/2003 | Sachdeva | ................ | A61C 7/00 433/24 |
| 7,845,938 B2 * | 12/2010 | Kim | ...................... | A61C 7/146 433/3 |
| 8,002,543 B2 * | 8/2011 | Kang | .................... | A61C 7/145 433/3 |
| 8,439,671 B2 * | 5/2013 | Cinader, Jr. | ........... | A61C 7/146 433/24 |
| 8,684,728 B1 * | 4/2014 | Wiesemann | ............. | A61C 3/00 433/3 |
| 2003/0003415 A1 * | 1/2003 | Kim | ...................... | A61C 7/146 433/3 |
| 2003/0224310 A1 * | 12/2003 | Andreiko | ............... | A61C 7/146 433/3 |
| 2004/0219471 A1 * | 11/2004 | Cleary | .................. | A61C 7/146 433/3 |
| 2004/0229185 A1 * | 11/2004 | Knopp | .................. | A61C 7/146 433/24 |
| 2005/0136370 A1 * | 6/2005 | Brennan | ................ | A61C 7/146 433/9 |
| 2005/0244790 A1 | 11/2005 | Kuperman | | |
| 2006/0121405 A1 * | 6/2006 | Hollard | .................... | A61C 7/02 433/3 |
| 2006/0223021 A1 * | 10/2006 | Cinader, Jr. | ........... | A61C 7/146 433/3 |
| 2006/0257821 A1 * | 11/2006 | Cinader, Jr. | ........... | A61C 7/146 433/213 |
| 2007/0031775 A1 * | 2/2007 | Andreiko | ............... | A61C 7/146 433/24 |
| 2007/0298364 A1 * | 12/2007 | Cinader, Jr. | ........... | A61C 7/146 433/3 |
| 2008/0233530 A1 * | 9/2008 | Cinader | ............... | A61C 19/004 433/9 |
| 2010/0279243 A1 * | 11/2010 | Cinader, Jr. | ........... | A61C 7/146 433/3 |
| 2013/0004910 A1 * | 1/2013 | Halbich | ................ | A61C 7/146 433/3 |
| 2013/0122443 A1 * | 5/2013 | Huang | ..................... | A61C 7/14 433/3 |
| 2013/0196279 A1 * | 8/2013 | Curiel | .................... | A61C 7/002 433/3 |
| 2014/0255864 A1 * | 9/2014 | Machata | ................ | A61C 7/146 433/3 |
| 2015/0305831 A1 * | 10/2015 | Cosse | ...................... | A61C 7/14 433/3 |
| 2015/0359610 A1 * | 12/2015 | Carrillo Gonzalez | . | A61C 7/146 433/3 |
| 2016/0000529 A1 * | 1/2016 | Kim | ...................... | A61C 7/146 433/3 |

FOREIGN PATENT DOCUMENTS

| | | |
|---|---|---|
| JP | 2008-043731 A | 2/2008 |
| JP | 2010-227607 A | 10/2010 |
| TW | 200936104 A | 9/2009 |

* cited by examiner

ORTHODONTIC DEVICE-SETTING TOOL

CROSS REFERENCE TO RELATED APPLICATIONS

This application is a national stage filing under section 371 of International Application No. PCT/JP2013/052524, filed on Feb. 5, 2013, and published in Japanese on Aug. 29, 2013, as WO 2013/125340 A1 and claims priority of Japanese application No. 2012-033587 filed on Feb. 20, 2012, the entire disclosure of these applications being hereby incorporated herein by reference.

TECHNICAL FIELD

The present invention relates to an orthodontic device-setting tool for three-dimensionally accurately disposing and anchoring an orthodontic device on a labial/buccal surface or a lingual surface of each tooth of a patient that undergoes orthodontic treatment.

BACKGROUND ART

Orthodontic treatment in dentistry is provided by adding a weak force to the teeth of a patient to facilitate change in tissues supporting the teeth and moving the teeth to respective desirable positions. There are many kinds of orthodontic devices used for moving the teeth. From among them, orthodontic devices called edgewise devices are broadly used, and such orthodontic devices are used by mounting a wire on brackets or buccal tubes.

In orthodontic treatment, an ideal occlusion as of the end of the orthodontic treatment is contemplated in consideration of, e.g., the biological background of, and the shapes of the teeth of, each patient, and then desired three-dimensional mounting positions for orthodontic devices are determined. Thus, in order to achieve an ideal alignment of the teeth, dentists provide treatment using a direct-bonding method to directly mount orthodontic devices to the teeth of a patient in their offices at the time of the start of orthodontic treatment or an indirect bonding method to determine positions for mounting orthodontic devices in advance using a setup model (stone model) created by making an impression of the alignment of the teeth of a patient with silicone and realigning the respective teeth based on the impression, and mount the orthodontic devices to the teeth of the patient.

In the direct bonding method, skills are required to mount orthodontic devices to respective correct positions in a plurality of teeth, and thus, the result of treatment depends on the level of the skills of the dentist, who is an operator. More specifically, for example, in order to mount orthodontic devices to 28 upper and lower teeth, while a dentist skilled in this treatment can mount an orthodontic device to each teeth in around two minutes, that is, the orthodontic devices to all the 28 teeth in about one hour, a dentist not skilled in this treatment has difficulty mounting the orthodontic devices to the correct positions, and even if he/she can mount the orthodontic devices to the correct positions, he/she takes more time, and thus, may require two or three hours, resulting in a large burden imposed on the patient resulting from being held for such long period of time. Also, for example, even a dentist skilled in this treatment sometimes fails to mount orthodontic devices to correct positions if he/she tries to mount the orthodontic devices more quickly, or depending on his/her mood or physical condition on the day, and thus, after all, the result of treatment is influenced by the dentist who is the practitioner.

On the other hand, in the indirect method, a setup model is created based on an impression made based on the alignment of the teeth of a patient, and thus, although it is said that much time can be taken to easily mount orthodontic devices to correct positions, an error may occur in dimensional accuracy depending on the level of the skills of the dental technician who is the creator of the setup model, which may cause problems such as floating-up of the orthodontic devices. Also, although the burden on a patient resulting from the patient being long held is reduced because orthodontic devices are created based on a setup model, the dentist or the dental technician takes much time to create orthodontic devices so as to mount the orthodontic devices to correct positions, and consequently, such method is hardly regarded as a simple method for dentists.

Therefore, for example, Japanese Patent Laid-Open No. 2008-43731 discloses an invention relating to a corrective appliance positioning jig including three or four corrective bracket support sections configured to hold respective corrective brackets specially designed to be attached to respective teeth in order for an orthodontist to dispose orthodontic devices to be attached to the teeth of a patient.

SUMMARY OF INVENTION

Technical Problem

However, the corrective appliance positioning jig described in Japanese Patent Laid-Open No. 2008-43731 includes a body having a surface corresponding to a crown of a tooth, and a structure that holds a corrective bracket, and the corrective bracket is directly attached to the tooth. Thus, it is necessary to design or cut a surface of a base of the corrective bracket that is to be attached to the tooth, according to the shape of a surface of the respective tooth, that is, it is necessary to specially create each corrective bracket, taking a lot of trouble in the corrective bracket creation.

Furthermore, since the corrective brackets and the corrective appliance positioning jig are separate bodies, when they are combined, the corrective brackets may be displaced from respective desired three-dimensional mounting positions for the corrective brackets. In such case, it is necessary to make minor adjustments such as cutting the surfaces of the bases of the corrective brackets that are to be mounted to the teeth.

Therefore, an object of the present invention is to provide an orthodontic device-setting tool that makes it possible to mount orthodontic devices such as corrective brackets without holding a patient for a long period of time and mount the orthodontic devices accurately at desired three-dimensional mounting positions for the orthodontic devices regardless of the level of the skills of the dentist who is the practitioner, and makes it possible to use even mass-produced general-purpose orthodontic devices, which are not orthodontic devices that have been specifically customized as to design, cut, etc., for individual patients.

Solution to Problem

In other words, an orthodontic device-setting tool according to the present invention is an orthodontic device-setting tool including: a fitting section including a fitting surface that covers and fits on at least one of an incisal margin, a dental cusp and an occlusal surface of a tooth; a foundation section including a back surface that adheres closely to a labial/buccal surface or a lingual surface of the tooth, and a front face that allows an orthodontic device to be anchored thereto, in a surface opposing the back surface; and a connecting section that connects the fitting section and the foundation section.

Also, in the orthodontic device-setting tool, based on information obtained by reading a three-dimensional shape of a teeth alignment using an optical method, the fitting surface of the fitting section and the back surface of the foundation section are shaped so as to closely adhere to the labial/buccal surface or the lingual surface of the tooth.

Also, the orthodontic device-setting tool includes a frame section that protrudes from the front face of the foundation section, and can fit with the orthodontic device.

Also, in the orthodontic device-setting tool stated in any of the above paragraphs, the connecting section is provided so as to provide a gap between the labial/buccal surface or the lingual surface of the tooth and the connecting section.

Also, in the orthodontic device-setting tool according to any of the above paragraphs, the fitting surface covers a proximal surface of the tooth.

Also, in the orthodontic device-setting tool according to any of the above paragraphs, the fitting section covers at least one of an incisal margin, a dental cusp or an occlusal surface of each of a plurality of teeth, and the foundation section is provided from a part of the fitting section so as to be attached to a labial/buccal surface or a lingual surface of each of one or more teeth of the teeth.

As stated above, the present invention makes it possible to mount orthodontic devices such as corrective brackets without holding a patient for a long period of time and mount the orthodontic devices accurately at desired three-dimensional mounting positions for the orthodontic devices regardless of the level of the skills of the dentist who is the practitioner, and makes it possible to use even mass-produced general-purpose orthodontic devices, which are not orthodontic devices that have been specifically customized as to design, cut, etc., for individual patients.

DESCRIPTION OF EMBODIMENTS

Embodiments of an orthodontic device-setting tool according to the present invention will be described in detail below. Since the below-described embodiments are specific examples that are preferable for carrying out the present invention, various technical limitations are provided; however, the present invention is not limited to these embodiments as long as no clear description that specifically limits the invention is included in the below description.

Figure 1:
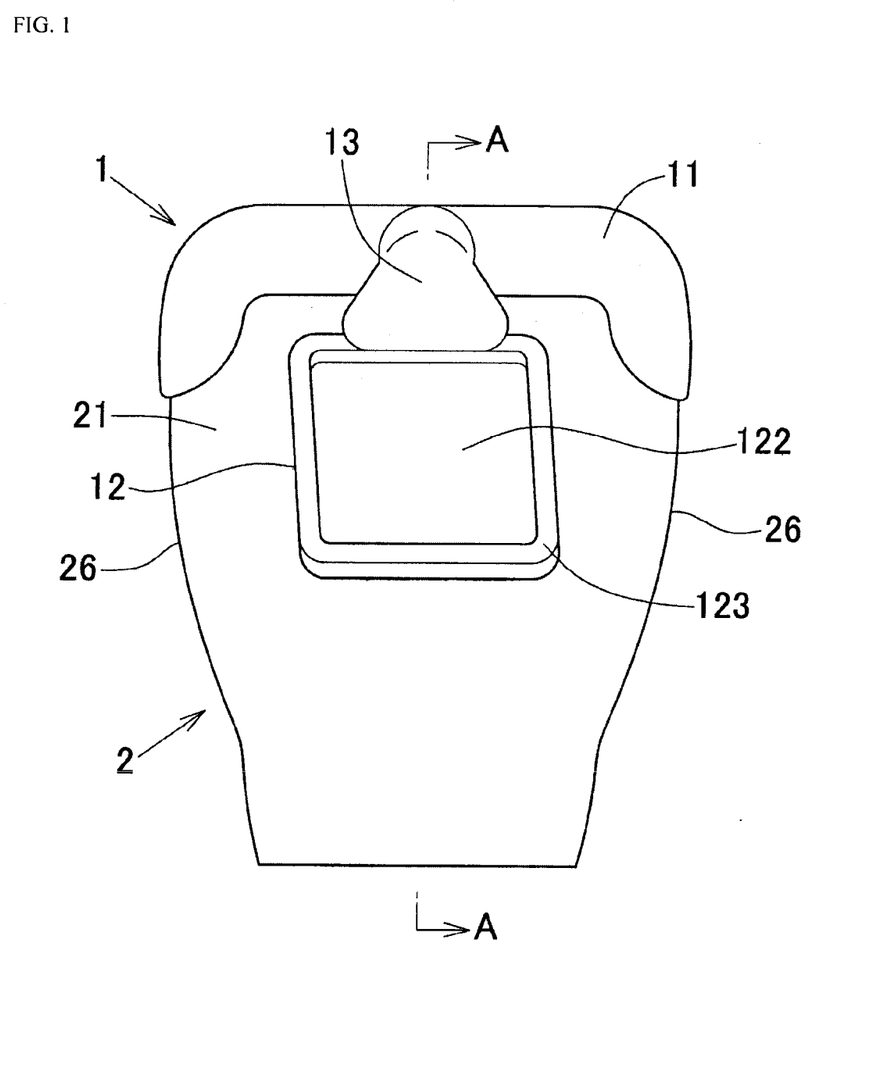
FIG. 1 is a cross-sectional view along line A-A of a state in which a first embodiment of the present invention is mounted to a tooth.
Figure 2:
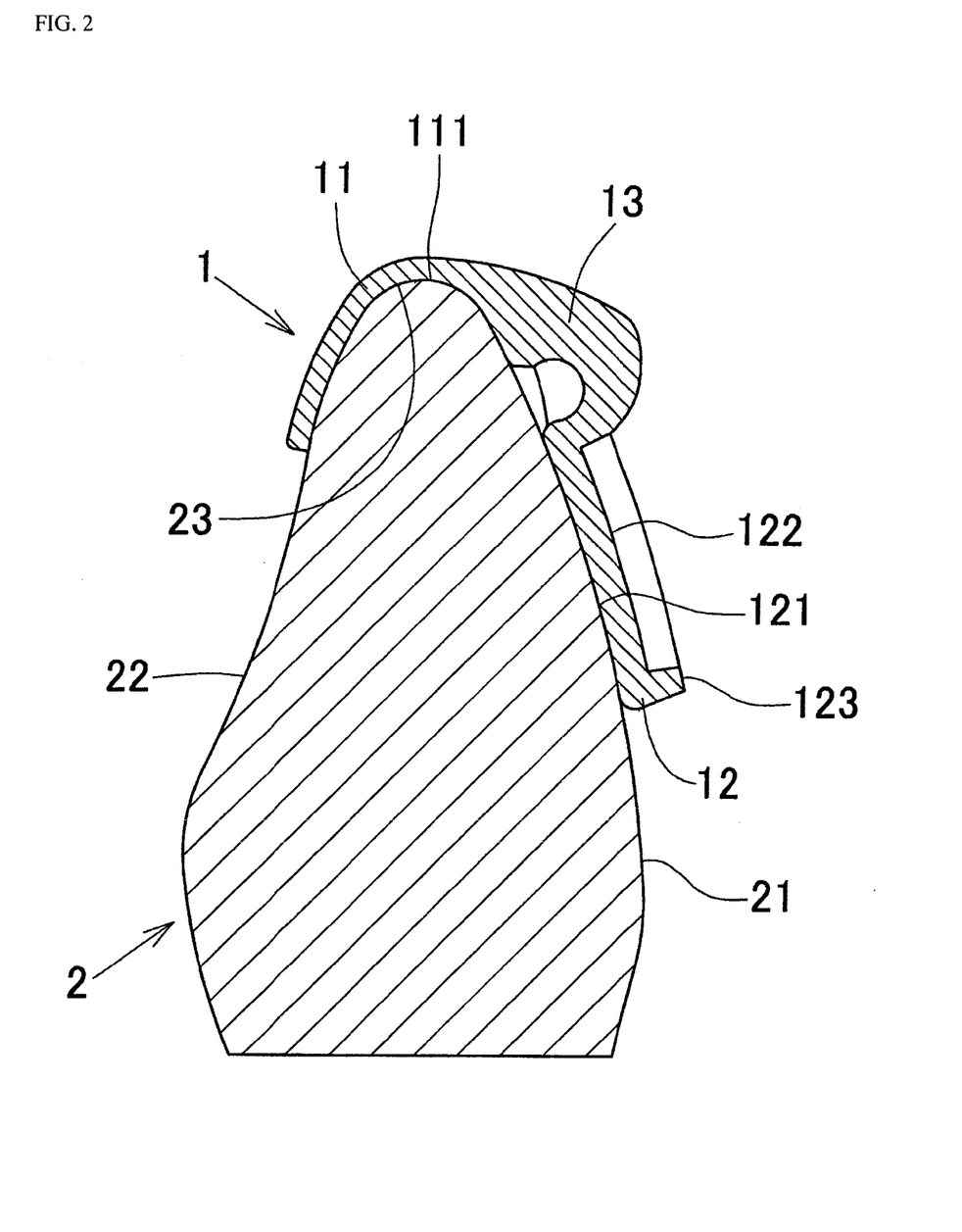
FIG. 2 is a left-side view of a state in which the first embodiment of the present invention is mounted to a tooth.

As illustrated in FIGS. 1 and 2, a first embodiment of an orthodontic device-setting tool (1) according to the present invention includes: a fitting section (11) including a fitting surface (111) that covers and fits on an incisal margin (23) of a tooth (2); a foundation section (12) including a back surface (121) that closely adheres to a labial/buccal surface (21) of the tooth (2) and a front face (122) that allows an orthodontic device (3) to be anchored thereto, in a surface opposing the back surface (121); and a connecting section (13) connecting the fitting section (11) and the foundation section (12).

More specifically, the fitting surface (111) provided on the inner side of the fitting section (11), which is a part of the orthodontic device-setting tool (1), covers the incisal margin (23), which is a part of one tooth that occludes with another tooth, and closely adheres to the incisal margin (23). The arch-like connecting section (13) connected to the fitting section (11) and providing a gap between the labial/buccal surface (21) of the tooth (2) and the connecting section (13) is connected to the fitting section (11) at one end thereof and to the foundation section (12) at the other end thereof. The foundation section (12) includes the back surface (121) that closely adheres to the labial/buccal surface (21) of the tooth (2), the front face (122) that allows the orthodontic device (3) to be anchored thereto, in the surface opposing the back surface (121), and a frame section (123) that protrudes from the front face (122) and fits with the orthodontic device (3). Although in FIGS. 1 and 2, the foundation section (12) of the orthodontic device-setting tool (1) is provided so as to closely adhere to the labial/buccal surface (21) of the tooth (2), the foundation section (12) may be provided so as to closely adhere to a lingual surface (22) of the tooth (2).

Figure 7:
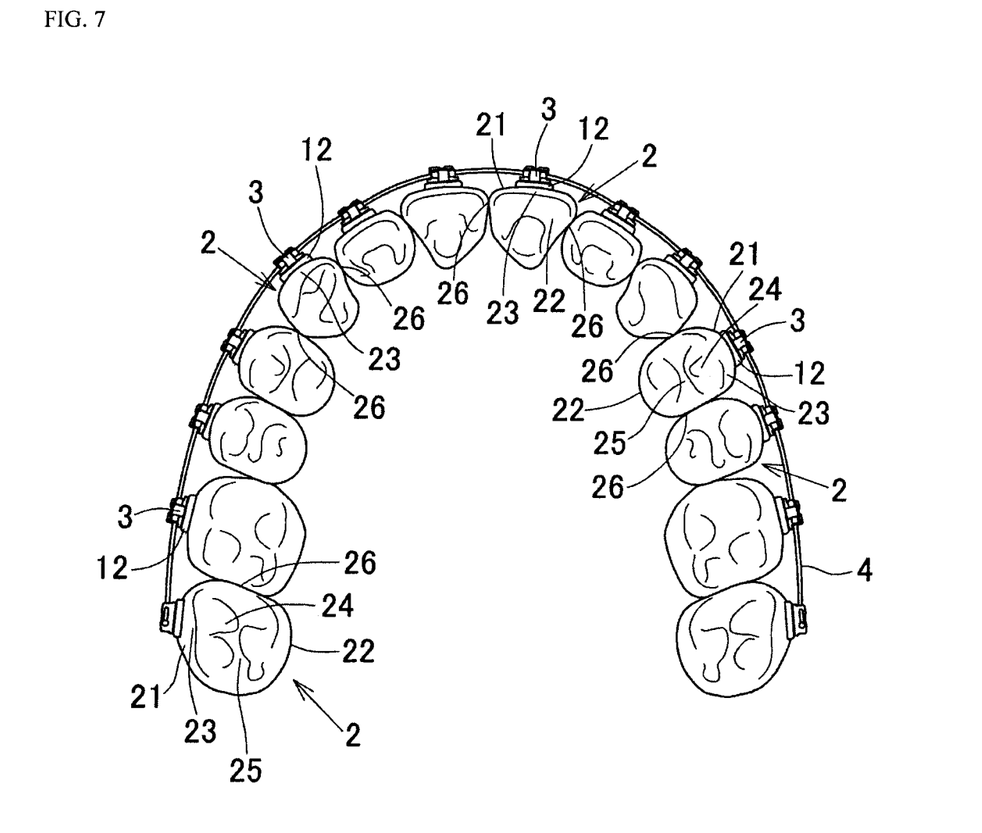
FIG. 7 is a diagram of a state after treatment is provided by passing a wire through corrective brackets mounted to a plurality of teeth using the first embodiment of the present invention.

The fitting section (11) has a shape obtained by cutting a substantially-round tube in half along an axis thereof and attaching a cover to each of opposite ends of a resulting half-round tube. The fitting surface (111) provided on the inner side of the fitting section (11) can cover and closely adhere to the incisal margin (23) of the tooth (2). Furthermore, the fitting surface (111) covers a part of the labial/buccal surface (21) around the incisal margin (23), the lingual surface (22) and proximal surfaces (26) between the teeth. Also, as described later, based on a surface shape of each of the incisal margin (23), and the labial/buccal surface (21) around the incisal margin (23), the lingual surface (22) and the proximal surfaces (26) between the teeth in information obtained by reading a three-dimensional shape of the tooth (2) using an optical method, the fitting surface (111) is formed so as to closely adhere to these surfaces. When used for each molar tooth, the fitting section (11) covers not only an incisal margin (23) but also a dental cusp (24) and an occlusal surface (25), which are illustrated in FIG. 7.

The foundation section (12) has a substantially-quadrangular flat plate-like shape. As described later, based on a surface shape of the labial/buccal surface (21) in the information obtained by reading the three-dimensional shape of the tooth (2) using an optical method, the back surface (121) is shaped so as to closely adhere to the labial/buccal surface (21). The front face (122) has a flat shape and includes a frame section (123) that protrudes so as to bulge from the front face (122) along outer edges thereof. The frame section (123) fits with a base section (31) of the orthodontic device (3) such as a corrective bracket, and even if the orthodontic device (3) is an orthodontic device (3) manufactured for general purposes, the orthodontic device (3) can be anchored to a position where the orthodontic device (3) should be fixed. Also, the front face (122) can be subjected to surface treatment so as to have patterned indentations for bonding force enhancement or may be designed in advance so as to have patterned indentations. Here, the shape of the foundation section (12) is not limited to the substantially quadrangular flat plate-like shape, and can be any of various shapes such as a substantially-round shape or a substantially-oval shape if such shape allows provision of the frame section (123) that can make the orthodontic device (3) be fitted therein. Furthermore, the shape of the frame section (123) is not limited to a shape surrounding the outer edges, and may be a shape in which a frame section (123) discontinues partway thereof, such as an letter L shape provided at each of four corners of the foundation section (12).

The connecting section (13) is connected to a side surface on the outer side of the fitting section (11), and on the opposite side, is connected to a side surface on the outer side of the frame section (123) of the foundation section (12), and furthermore, is formed in an arch-like shape so as to provide a gap between the labial/buccal surface (21) of the tooth (2) and the connecting section (13). It is preferable to provide the connecting section (13) so as to provide a gap between the labial/buccal surface (21) and the connecting section (13) such as having a circular-arc or angular arch shape, which, however, does not prevent the connecting section (13) from being provided to provide no gap between the labial/buccal surface (21) and the connecting section (13).

Next, a method for creating the first embodiment of the orthodontic device-setting tool (1) according to the present invention will be described.

In other words, as a first step, an impression taken of a patient before orthodontic treatment or a tooth alignment model fabricated based on the impression is read using a three-dimensional optical scanner to obtain three-dimensional data on a tooth alignment of a patient as electronic information. For the impression used here, it is preferable to use a high-precision material, that is, a material exhibiting a small rate of contraction and expansion when cured such as silicone impression material. For the tooth alignment model fabricated based on the impression, it is preferable to use, e.g., plaster having an expansion rate of less than 0.1%. Consequently, neither difference depending on the experience of the dentist or the dental technician nor difference in work accuracy occurs, enabling fabrication of the orthodontic device-setting tool (1) that enables the orthodontic device (3) to be correctly mounted to the tooth (2) of the patient.

Then, as a second step, based on the three-dimensional data unique to the patient, which has been obtained in the first step, and in consideration of, e.g., the biological background and the shape of the teeth of the patient, an electronic setup model having an ideal occlusion after orthodontic treatment (hereinafter referred to as "electronic setup model") is obtained using commercially-available software such as 3DTXer sold by Biodent Corporation.

Then, as a third step, an electronic orthodontic wire to be used by the dentist is set on the labial/buccal surface or the lingual surface of each tooth obtained as electronic information on the electronic setup model, via a computer.

Then, as a fourth step, positions for mounting respective orthodontic devices that fit with the wire set in the third step are set for the respective teeth of the plurality of teeth obtained as the electronic information, via the computer. The three-dimensional data on the orthodontic devices handled via the computer is one obtained based on arbitrary devices that are sold by any of various manufacturers and actually used by the operator such as a dentist.

Then, as a fifth step, data on a space existing between the labial/buccal surface or the lingual surface of each tooth of the electronic setup model and a mounting surface for mounting an orthodontic device, which is set at the corresponding mounting position (hereinafter referred to as "tooth surface-mounting surface space information") is obtained.

Then, as a sixth step, based on the tooth surface-mounting surface space information, information on an orthodontic device-setting tool including information on a foundation section that fills the space between the labial/buccal surface or the lingual surface of each tooth and an orthodontic device mounting surface set at the corresponding mounting position (hereinafter referred to as "orthodontic device-setting tool information") is created via the computer. In particular, a thickness of the foundation section is not uniform but varies depending on the part of the foundation section; however, from the orthodontic device mounting positions set in the fourth step and the electronic setup model, a distance between the mounting surface of the orthodontic device and the labial/buccal surface or the lingual surface of each tooth is uniquely determined, and thus, the thickness of each part of the foundation section is also uniquely determined.

Then, as a seventh step, based on data on surface shapes of at least one of an incisal margin, a dental cusp and an occlusal surface of a tooth and the labial/buccal surface or the lingual surface of the tooth and proximal surfaces between the teeth around at least one of the incisal margin, the dental cusp and the occlusal surface, information on a fitting section including a fitting surface that fits on them is provided to the orthodontic device-setting tool information.

Then, as an eighth step, furthermore, information on an arch-like connecting section, which is provided between the foundation section and the fitting section so as to provide a gap between the labial/buccal surface (21) of the tooth (2) and the connecting section, is provided to the orthodontic device-setting tool information. This is intended to remove an extra portion of an adhesive that has run over from a back surface (121) of the foundation section (12) and to easily remove the fitting section (11) without damaging the labial/buccal surface (21) of the tooth (2) after mounting the orthodontic device (3).

Then, as a ninth step, furthermore, information on a frame section that protrudes from a front face of the foundation section at outer edges of the foundation section based on the three-dimensional data on the orthodontic device so as to allow the orthodontic device (3) to be fit therein is provided to the orthodontic device-setting tool information.

Consequently, orthodontic device-setting tool information including the information on the foundation section, the information on the fitting section, the information on the arch-like connecting section and the information on the frame section that protrudes from the front face of the foundation section is finally obtained.

Based on the finally-obtained orthodontic device-setting tool information, the orthodontic device-setting tool (1) is fabricated by being carved out from a resin block including a resin, for example, a resin block obtained by polymerizing, e.g., Unifast III manufactured by K.K. GC, using a cutting apparatus such as a three-dimensional milling machine. Also, based on the finally-obtained orthodontic device-setting tool information, the orthodontic device-setting tool (1) may be fabricated by an additive fabrication apparatus, using a material such as a metal, a ceramic or a resin.

Also, as described above, although it is preferable to fabricate the orthodontic device-setting tool (1) based on finally-obtained orthodontic device-setting tool information created from an electronic setup model via a personal computer, the orthodontic device-setting tool (1) may be fabricated based on a setup model fabricated as an actual model from an impression taken of a patient before orthodontic treatment.

With the orthodontic device-setting tool (1) obtained as described above, a positional relationship between the fitting section (11) and the foundation section (12) of the orthodontic device-setting tool (1) and the tooth (2) is uniquely determined via the connecting section (13) connected to the fitting section (11) and the foundation section (12), making it possible to accurately mount the orthodontic device (3) such as a corrective bracket to a desired three-dimensional mounting position for the orthodontic device regardless of the level of the skills of the dentist who is the practitioner. Also, the orthodontic device (3) can be mounted without holding the patient for a long period of time.

Then, the base section (31) of the orthodontic device (3) is not directly mounted to the tooth (2), but the base section (31) of the orthodontic device (3) is mounted to the foundation section (12) after the foundation section (12) of the orthodontic device-setting tool (1) is made to closely adhere to the tooth (2), and thus, even mass-produced general-purpose orthodontic devices which are not orthodontic devices specifically customized as to design, cut, etc., for individual patients, can be used. As described above, even general-purpose orthodontic devices can be used, and thus, just fabrication of the orthodontic device-setting tools (1) enables suppression of costs for processing orthodontic devices, and consequently reduction in medical expense for patients.

With the above-described orthodontic device-setting tool (1) shaped so that the fitting surface (111) of the fitting section (11) and the back surface (121) of the foundation section (12) closely adhere to the labial/buccal surface (21) or the lingual surface (22) of the tooth (2), based on information obtained by reading a three-dimensional shape of a tooth alignment by an optical method, the orthodontic device-setting tool (1) provides close adhesion with accuracy that is higher than that of an orthodontic device-setting tool fabricated based on a tooth alignment model fabricated as an actual model from an impression taken of a patient before orthodontic treatment, enabling prevention of a failure such as the foundation section (12) coming off or floating up from the labial/buccal surface (21) or the lingual surface (22) of the tooth (2) during the orthodontic treatment. Also, for dentists or dental technicians, the need to cut a mounting surface (32) of the orthodontic device (3) for minor adjustment is eliminated, enabling easy mounting of the orthodontic device (3).

Also, with the orthodontic device-setting tool (1) including the frame section (123) that protrudes from the front face (122) of the foundation section (12) and fits with the orthodontic device (3) such as a corrective bracket, a mounting position for the orthodontic device (3) in the foundation section (12) is uniquely determined, enabling even an operator that have never provided orthodontic treatment to easily mount the orthodontic device (3).

Also, with the orthodontic device-setting tool (1) in which the connecting section (13) is provided so as to provide a gap between the labial/buccal surface (21) or the lingual surface (22) of the tooth (2) and the connecting section (13), even if an adhesive applied to the back surface (121) of the foundation section (12) runs out from the foundation section (12) when the back surface (121) is bonded to the labial/buccal surface (21) or the lingual surface (22) of the tooth (2), the part of the adhesive that has run out can be removed from an entire outer periphery of the foundation section (12). Thus, even if a liquid adhesive is used, the adhesive does not stick to the connecting section (13), and when the fitting section (11) and the connecting section (13) are removed from the foundation section (12) after the foundation section (12) is bonded, the connecting section (13) can easily be removed. Also, when the fitting section (11) and the connecting section (13) are removed from the foundation section (12) after the foundation section (12) is bonded, the fitting section (11) and the connecting section (13) can be cut off using, e.g., a dental cutting appliance without damaging the labial/buccal surface (21) or the lingual surface (22) of the tooth (2).

Also, with the above-described orthodontic device-setting tool (1) in which the fitting surface (111) covers the proximal surfaces (26) of the tooth (2), the area of the fitting surface (111) that closely adheres to at least one of the incisal margin (23), the dental cusp (24) and the occlusal surface (25) of the tooth (2) increases, whereby accuracy of positioning the fitting section (11) relative to at least one of the incisal margin (23), the dental cusp (24) and the occlusal surface (25) of the tooth (2) is further enhanced, enabling further enhancement in accuracy of positioning the foundation section (12) relative to the labial/buccal surface (21) or the lingual surface (22) of the tooth (2).

Next, a method of using the first embodiment of the orthodontic device-setting tool (1) according to the present invention will be described.

As illustrated in FIGS. 1 and 2, an adhesive is applied to the back surface (121) of the foundation section (12) of the orthodontic device-setting tool (1) fabricated based on the orthodontic device-setting tool information described above and then the fitting section (11) is fitted on the incisal margin (23) of the tooth (2) of a patient. Here, an extra portion of the adhesive that has run out from the back surface (121) of the foundation section (12) is removed. Also, if the used adhesive is a photopolymerization type resin containing a compound having an acrylate group, the adhesive is polymerized by an irradiator such as a light irradiator or an LED irradiator. Also, if the used adhesive is a chemical polymerization type resin containing, e.g., a compound having an acrylate group, the adhesive is left still for polymerization. As necessary, before the back surface (121) of the foundation section (12) is bonded, a primer, which is a material containing, e.g., a compound having a photopolymerization property and a material that facilitates curing may be applied to a part of the labial/buccal surface (21) of the tooth (2) to which the back surface (121) of the foundation section (12) is bonded, for facilitating curing of the adhesive and enhancing the close adhesion.

Figure 3:
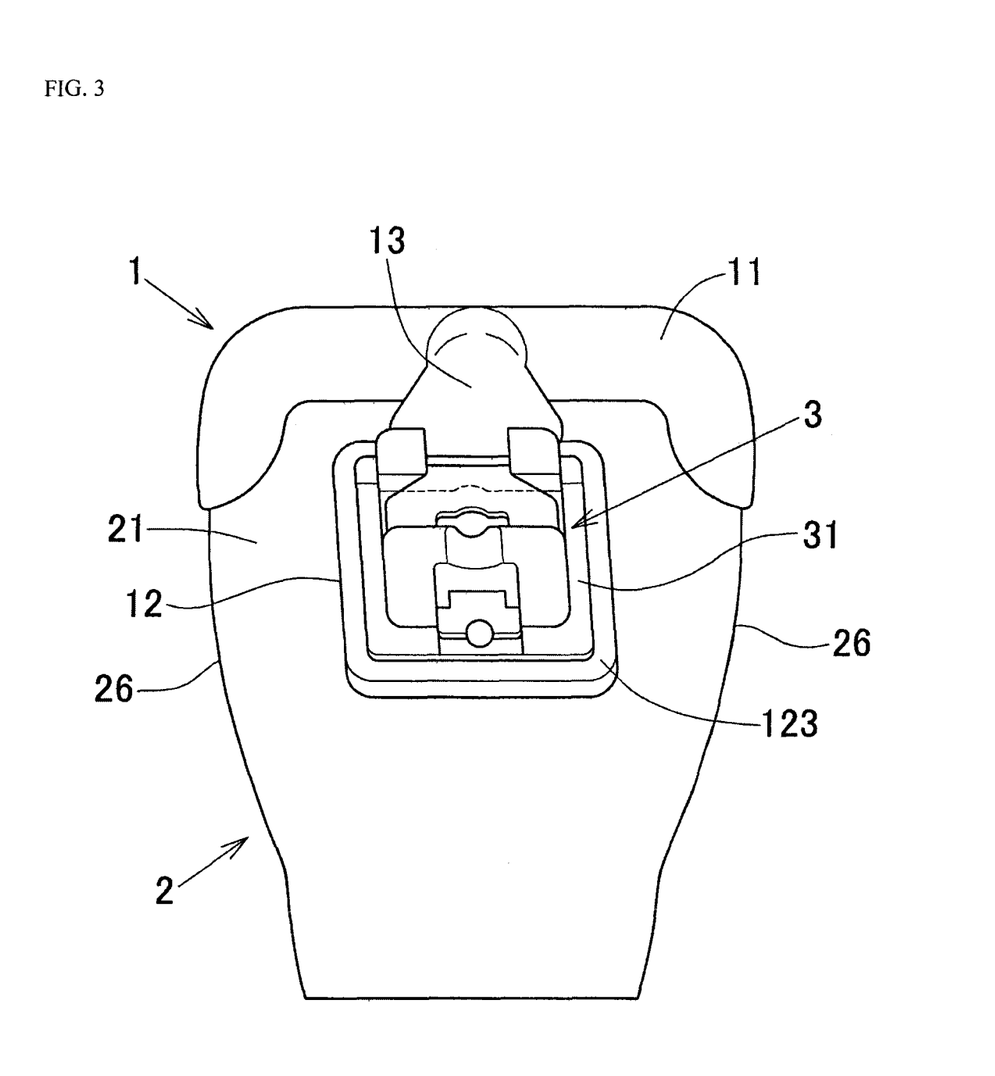
FIG. 3 is a front view of a state in which a corrective bracket is fixed to the state in FIG. 1.
Figure 4:
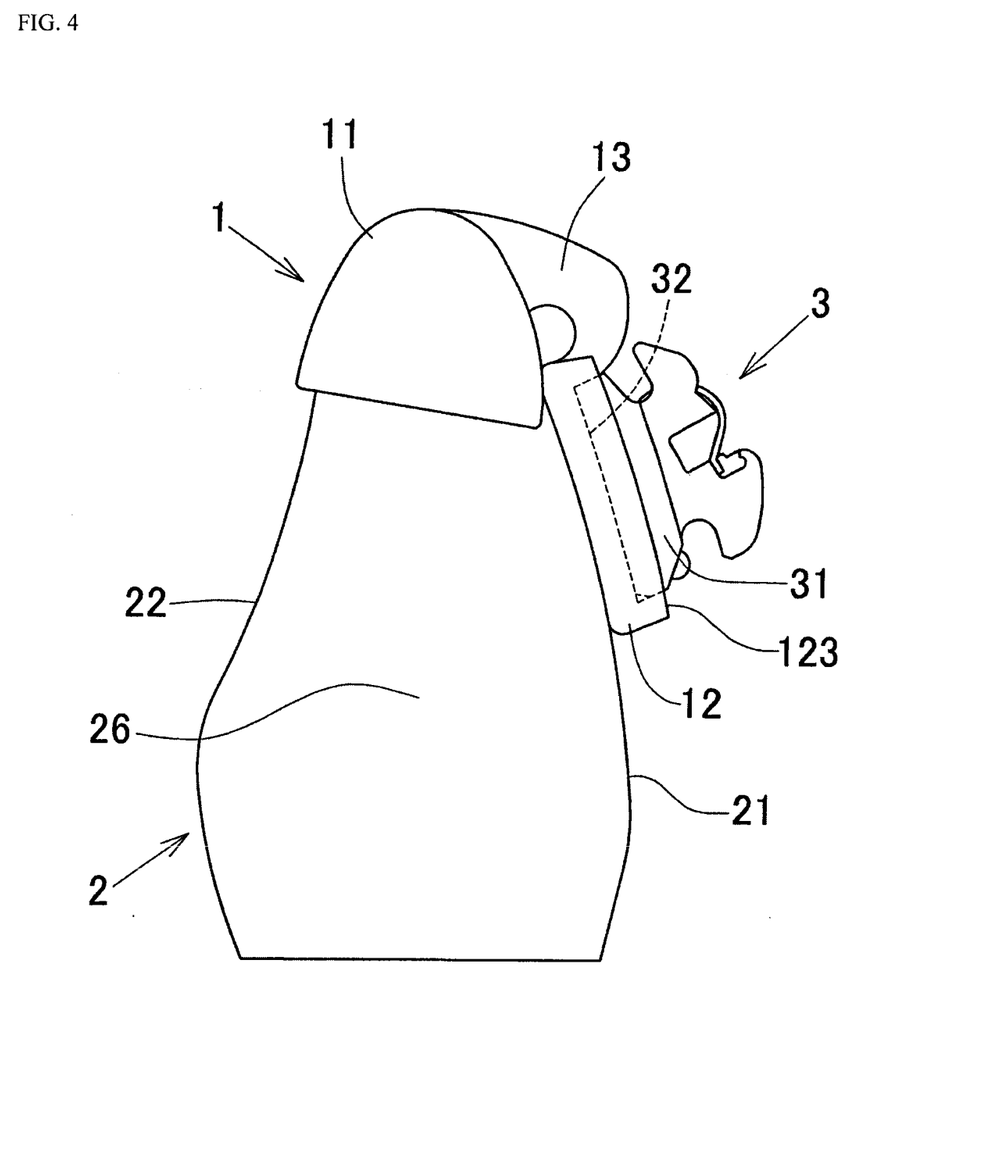
FIG. 4 is a left-side view of a state in which the corrective bracket is fixed to the state in FIG. 1.

Then, as illustrated in FIGS. 3 and 4, an adhesive is applied to the mounting surface (32) of the base section (31) of the orthodontic device (3) and then the orthodontic device (3) is fitted in the frame section (123) of the foundation section (12) to bond the orthodontic device (3) to the front face (122) of the foundation section (12). Here, an extra portion of the adhesive that has run out from between the base section (31) of the orthodontic device (3) and the frame section (123) is removed. Also, if the used adhesive is a photopolymerization type resin containing a compound having an acrylate group, the adhesive is polymerized by an irradiator such as a light irradiator or an LED irradiator.

Also, if the used adhesive is a chemical polymerization type resin containing, e.g., a compound having an acrylate group, the adhesive is left still for polymerization. As necessary, before the mounting surface (32) of the base section (31) of the orthodontic device (3) is bonded, a primer, which is a material containing, e.g., a compound having a photopolymerization property and a material that facilitates curing, may be applied to the front face (122) of the foundation section (12) for facilitating curing of the adhesive and enhancing the close adhesion. Although for the orthodontic device (3), Tomy International Inc.'s Clippy (registered trademark) C is indicated in, e.g., FIGS. 3 and 4, the orthodontic device (3) is not limited to such product and any of various brackets, buccal tubes, etc., can be used.

Figure 5:
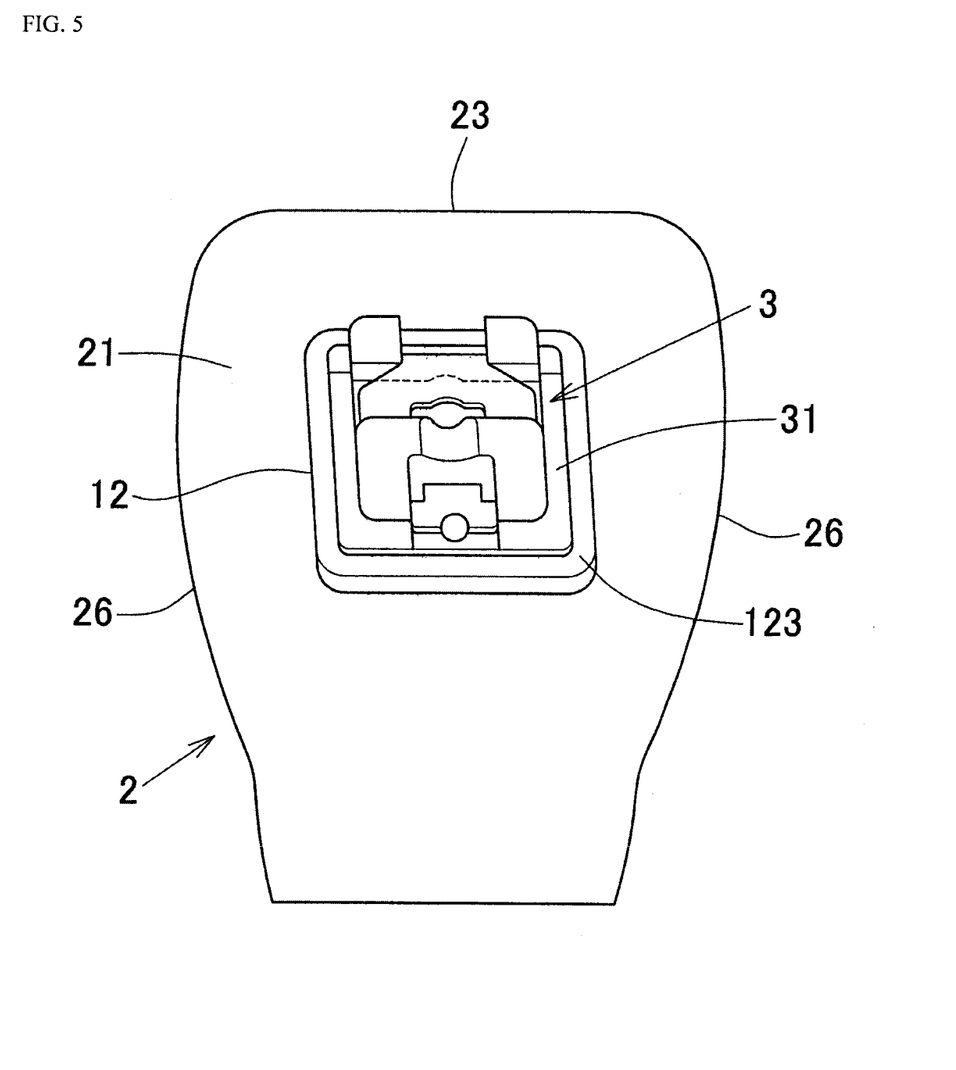
FIG. 5 is a front view of a state in which a fitting section and a connecting section have been removed from the state in FIG. 3.
Figure 6:
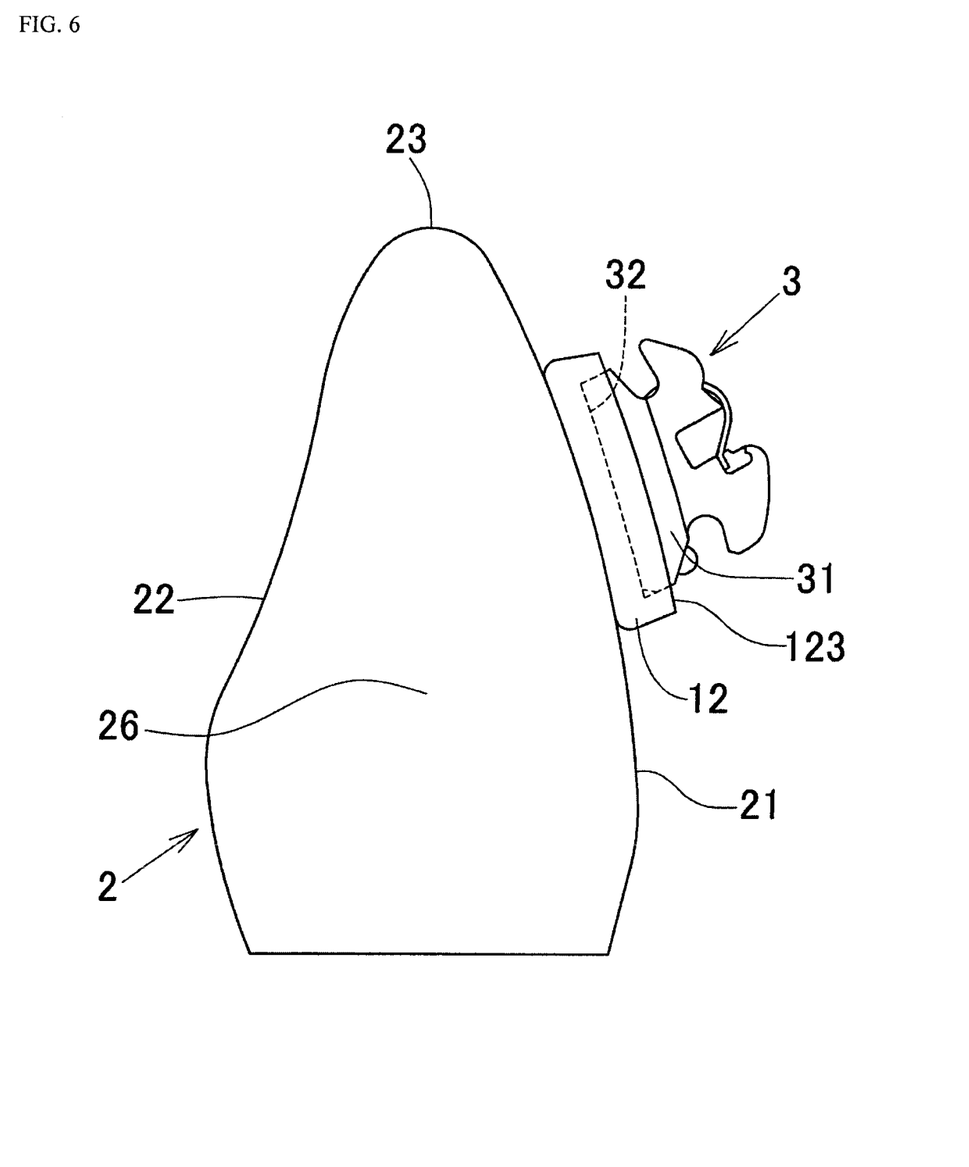
FIG. 6 is a left-side view of a state in which a fitting section and a connecting section have been removed from the state in FIG. 3.

Then, as illustrated in FIGS. 5 and 6, a boundary or a part around the boundary between the connecting section (13) and the foundation section (12) of the orthodontic device-setting tool (1) is cut off using any of various dental cutting appliances to remove the fitting section (11) and the connecting section (13). For easy cutting, e.g., a notch may be provided in the boundary between the connecting section (13) and the foundation section (12).

Then, a wire (4) is passed through a plurality of the orthodontic devices (3) mounted similarly to the above and anchored, thereby the work being ended. Here, the procedure from the mounting of the orthodontic devices (3) to the removal of the fitting section (11) and the connecting section (13) may be reversed. In other words, the orthodontic devices (3) may be mounted after the boundary or the part around the boundary between the connecting section (13) and the foundation section (12) of each orthodontic device-setting tool (1) is cut off using any of various cutting devices to remove the fitting section (11) and the connecting section (13).

FIG. 7 illustrates a state of a tooth alignment when orthodontic treatment is finished. As the orthodontic devices (3), a bracket is provided on the labial/buccal surface side of each of central incisors, lateral incisors, canines, first premolar teeth, second premolar teeth and first molar teeth, and a buccal tube is provided on the labial/buccal surface side of each of second molar teeth. The fitting sections (11) that have been cut off had covered respective incisal margins (23) of the central incisors, the lateral incisors and the canines, and had covered not only the incisal margins (23) but also dental cusps (24) and occlusal surfaces (25) of the respective molar teeth.

Figure 8:
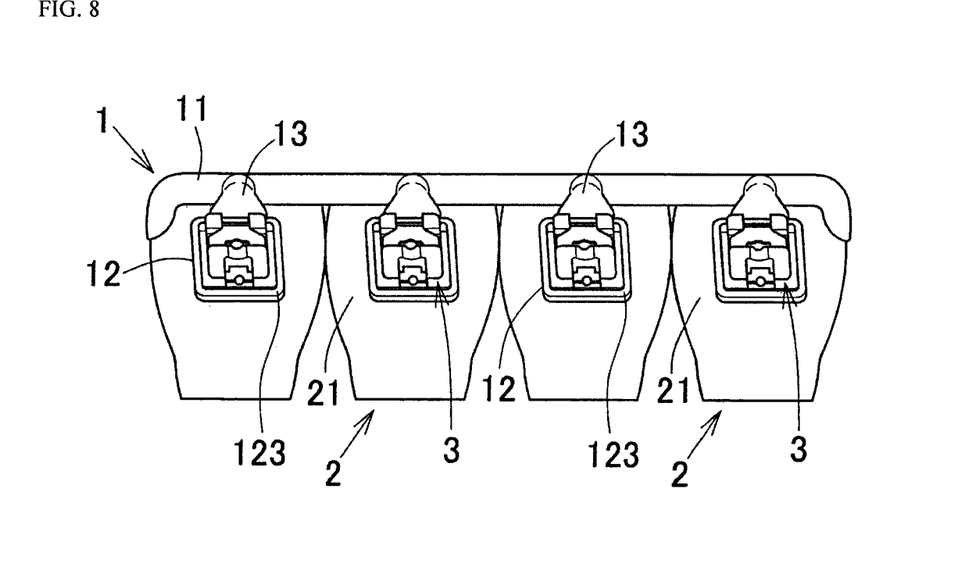
FIG. 8 is a front view of a state in which corrective brackets are fixed to a second embodiment of the present invention.

As illustrated in FIG. 8, a second embodiment of the orthodontic device-setting tool (1) according to the present invention is similar to the first embodiment except the point that a fitting section (11) in the first embodiment fits on at least one of an incisal margin, a dental cusp and an occlusal surface (not illustrated) of each of a plurality of teeth (2). A plurality of foundation sections (12) are positioned on only labial/buccal surfaces (21) or lingual surfaces (22) of the teeth (2). Although in FIG. 8, a fitting section (11) fits on at least one of an incisal margin, a dental cusp and an occlusal surface (not illustrated) of each of four teeth (2), the fitting section (11) may be configured so as to fit on a plurality of arbitrary teeth, or may also be configured so as to cover all of fourteen upper teeth or all of fourteen lower teeth.

Although in FIG. 8, the fitting section (11) is illustrated as a single-piece body, the fitting section (11) may have a configuration formed by connecting a plurality of parts. For example, more specifically, the fitting section (11) may include a plurality of parts with respective interdental sites as partitions, and end portions of each of the parts may have a shape such as a projection or recess shape so that the end portions can be joined to corresponding end portions of other adjacent parts. Furthermore, a member having a shape such as a projection or recess shape may be provided so as to extend from the fitting section (11) of the orthodontic device-setting tool (1) according to the first embodiment, and the extension section may engage with an extension section of the fitting section (11) of another adjacent orthodontic device-setting tool (1), whereby the fitting sections (11) of the individual orthodontic device-setting tools (1) may be joined to one another, forming one large fitting section (11) in FIG. 8.

Figure 9:
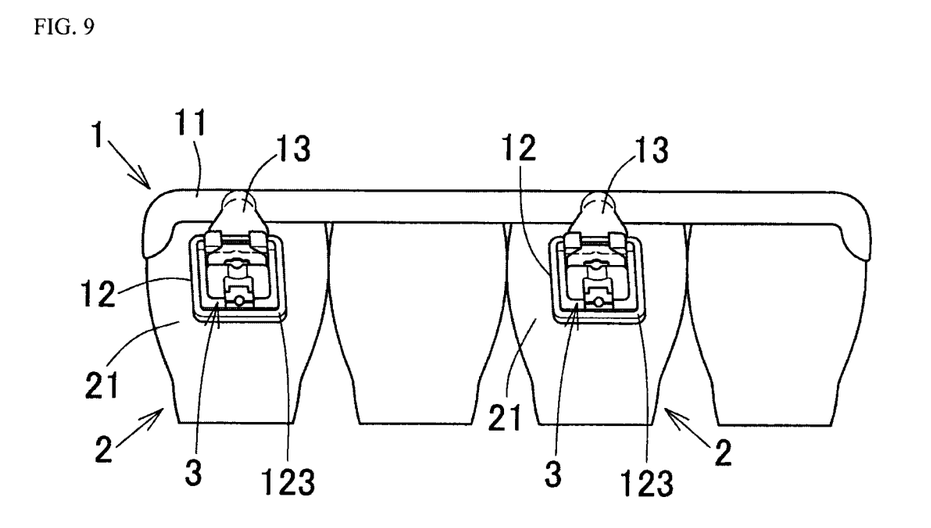
FIG. 9 is a front view of a state in which corrective brackets are fixed to a third embodiment of the present invention.

As illustrated in FIG. 9, a third embodiment of the orthodontic device-setting tool (1) according to the present invention is similar to the second embodiment except the point that the connecting section (13) and the foundation section (12) in the second embodiment are omitted at each of positions of arbitrary teeth (2). A plurality of the foundation sections (12) are positioned on only the labial/buccal surfaces (21) or the lingual surfaces (22) of the teeth (2). Also, as with the second embodiment, the fitting sections (11) may be configured so as to fit on a plurality of arbitrary teeth or may be configured to fit on all of fourteen upper teeth or all of fourteen lower teeth. For a-teeth already located at an ideal position when an electronic setup model having an ideal occlusion is created, the connecting section (13) and the foundation section (12) for the position can be omitted.

Although in FIG. 9, the fitting section (11) is illustrated as a single-piece body, the fitting section (11) may have a configuration formed by connecting a plurality of parts. For example, more specifically, the fitting section (11) includes a plurality of parts with respective interdental sites as partitions, and end portions of each of the parts may have a shape such as a projection or recess shape so that the end portions can be joined to corresponding end portions of other adjacent parts. Furthermore, a member having a shape such as a projection or recess shape may be provided so as to extend from the fitting section (11) of the orthodontic device-setting tool (1) according to the first embodiment, and the extension section may engage with an extension section of the fitting section (11) of another adjacent orthodontic device-setting tool (1), whereby the fitting sections (11) of the individual orthodontic device-setting tools (1) may be joined to one another, forming one large fitting section (11) in FIG. 9.

The invention claimed is:
1. An orthodontic device-setting tool comprising:
a fitting section including a fitting surface that covers and fits on at least one of an incisal margin, a dental cusp and an occlusal surface of a tooth;
a foundation section including a back surface that faces inwardly towards and adheres closely to a labial/buccal surface or a lingual surface of the tooth, and a front face that faces outwardly away from the labial/buccal surface or the lingual surface of the tooth and anchors an orthodontic device to the foundation section, at a mounting surface of the orthodontic device opposing the front face;
a connecting section that connects the fitting section and the foundation section;
a frame section that protrudes outwardly from the front face of the foundation section along outer edges of the front face, and accommodates the orthodontic device within the frame section; and wherein the orthodontic device is externally mounted by the frame section to the foundation section rather than directly mounted to the tooth, and the foundation section has a uniquely determined thickness correlated to a predefined desired distance between the mounting surface of the orthodontic device and the labial/buccal surface or the lingual surface of the tooth.

2. The orthodontic device-setting tool according to claim 1, wherein the connecting section provides a gap between the labial/buccal surface or the lingual surface of the tooth and the connecting section.

3. The orthodontic device-setting tool according to claim 2, wherein the fitting surface covers a proximal surface of the tooth.

4. The orthodontic device-setting tool according to claim 2, wherein the fitting section covers at least one of an incisal margin, a dental cusp or an occlusal surface of each of a plurality of teeth, and the foundation section is provided from a part of the fitting section so as to be attached to a labial/buccal surface or a lingual surface of each of one or more teeth of the plurality of teeth.

5. The orthodontic device-setting tool according to claim 1, wherein the fitting surface covers a proximal surface of the tooth.

6. The orthodontic device-setting tool according to claim 1, wherein the fitting section covers at least one of an incisal margin, a dental cusp or an occlusal surface of each of a plurality of teeth, and the foundation section is provided from a part of the fitting section so as to be attached to a labial/buccal surface or a lingual surface of each of one or more teeth of the plurality of teeth.

7. An orthodontic device-setting tool comprising:
a fitting section including a fitting surface that covers and fits on at least one of an incisal margin, a dental cusp and an occlusal surface of a tooth;
a foundation section including a back surface that faces inwardly towards and adheres closely to a labial/buccal surface or a lingual surface of the tooth, and a front face that faces outwardly away from the labial/buccal surface or the lingual surface of the tooth and anchor an orthodontic device to the foundation section, at a mounting surface of a corrective bracket opposing the front face;
a connecting section that connects the fitting section and the foundation section;
a frame section that protrudes outwardly from the front face of the foundation section along outer edges of the front face, and accommodates the corrective bracket within the frame section; and
wherein the corrective bracket is externally mounted by the frame section to the foundation section rather than directly mounted to the tooth, and the foundation section has a uniquely determined thickness correlated to a predefined desired distance between the mounting surface of the corrective bracket and the labial/buccal surface or the lingual surface of the tooth.

8. The orthodontic device-setting tool of claim 7, in combination with at least one more said orthodontic device-setting tool, each tool being adapted to be disposed on respective different teeth of a patient.

9. The combination of claim 8, wherein at least some of the respective different teeth share a common fitting section.

* * * * *